United States Patent [19]

Crout et al.

[11] Patent Number: 6,069,272
[45] Date of Patent: *May 30, 2000

[54] SIMPLIFIED METHOD FOR THE PRODUCTION OF VINYL GLYCINE (2-AMINOBUT-3-ENOIC ACID) AND A CONVENIENT RESOLUTION OF A DERIVATIVE

[75] Inventors: David Herbert George Crout, Cannon Park; Keith Oliver Hallinan, Bedworth, both of United Kingdom

[73] Assignee: Hoechst Aktiengesellschaft, Frankfurt am Main, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/848,568

[22] Filed: Apr. 28, 1997

Related U.S. Application Data

[63] Continuation of application No. 08/618,086, Mar. 19, 1996, abandoned, which is a continuation of application No. 08/355,228, Dec. 9, 1994, abandoned, which is a continuation of application No. 07/876,631, May 1, 1992, abandoned.

[30] Foreign Application Priority Data

Mar. 9, 1992 [EP]  European Pat. Off. .............. 92103979

[51] Int. Cl.[7] .................................................. C07C 229/00
[52] U.S. Cl. ........................................... 562/574; 435/106
[58] Field of Search .................... 562/574, 526; 435/106

[56] References Cited

U.S. PATENT DOCUMENTS

| | | | |
|---|---|---|---|
| 2,479,662 | 8/1949 | Albertson et al. ...................... | 562/574 |
| 4,275,220 | 6/1981 | Patchett et al. ........................... | 560/35 |
| 4,347,375 | 8/1982 | Patchett et al. .......................... | 548/344 |
| 4,751,296 | 6/1988 | Miller ...................................... | 540/355 |
| 4,806,680 | 2/1989 | Taub et al. .............................. | 562/574 |
| 4,950,788 | 8/1990 | Farrar et al. ............................. | 562/598 |

OTHER PUBLICATIONS

March, *Advanced Organic Chemistry*, John Wiley & Sons (1985), pp. 792–793, 981–982.

R.R. Rando, "Mechanisms of Action of Naturally Occurring Irreversible Enzyme Inhibitors," Accounts of Chemical Research, 8(8):281–288 (1975).

Havlicek et al., "Synthesis of beta, gamma–Unsaturated alpha–amino Acids," Collection of Czechoslovak Chemical Communications, 56(6):1365–1399 (1991).

G. Kruger, "Aminocarbonsaure und deren Drivate," Methoden der Organischen Chemie, Houben–Weyl, vol. E5, part 1, pp. 526–530 (1985).

W.H. Graham, "A General Synthesis of α–Amino Acid Orthoesters From Nitriles Via . . . ," Tetrahedron Letters No. 27, pp. 2223–2225 (1969).

Partington, et al., The Synthesis of $^{14}$C–Labeled . . . , Journal of Labelled Compounds and Radiopharmaceuticals, vol. XIV, No. 2, pp. 223–229 (1978).

*Primary Examiner*—Michael L. Shippen
*Attorney, Agent, or Firm*—Finnegan, Henderson, Farabow, Garrett & Dunner, L.L.P.

[57] ABSTRACT

The invention relates to a three-step synthesis of vinyl glycine (1) using a cheap, commercially available starting material (3-butenenitrile (2)) and using cheap, simple reagents. Also disclosed is a convenient optical resolution of the N-tert.butyloxycarbonyl derivative by papain-catalyzed enantioselective esterification in a two-phase system.

5 Claims, No Drawings

6,069,272

SIMPLIFIED METHOD FOR THE PRODUCTION OF VINYL GLYCINE (2-AMINOBUT-3-ENOIC ACID) AND A CONVENIENT RESOLUTION OF A DERIVATIVE

This is a continuation of application Ser. No. 08/618,086, filed Mar. 19, 1996, abandoned; which is a continuation of application Ser. No. 08/355,228 filed Dec. 9, 1994, abandoned; which is a continuation of application Ser. No. 07/876,631, filed May 1, 1992, abandoned.

The invention relates to a three-step synthesis of vinyl glycine (1) using a cheap, commercially available starting material (3-butenenitrile (2)) and using cheap, simple reagents. Also disclosed is a convenient optical resolution of the N-tert.butyloxycarbonyl derivative by papain-catalyzed enantioselective esterification in a two-phase system.

Vinyl glycine, a non-protein amino acid, has been isolated from fungi and has been shown to inhibit a number of enzymes. [R. Rando, Accounts of Chemical Research 8, 281 (1975)]. Because of its biological activity, vinyl glycine has been the subject of many synthetic studies since it was first prepared in 1974. A review including synthetic approaches to vinyl glycine has recently been published [L. Havlicek and J. Hanus, Collect. Czech. Chem. Commun. 56, 1365 (1991)]. Most of the described procedures for the preparation of vinyl glycine require multistep reaction sequences, often involving tedious protection and deprotection techniques.

The instant invention concerns a new and surprisingly simple method for the production of vinyl glycine as shown in the Reaction Scheme 1 below and is described below. The process for the synthesis of racemic vinyl glycine is quite straightforward and does not require protective groups.

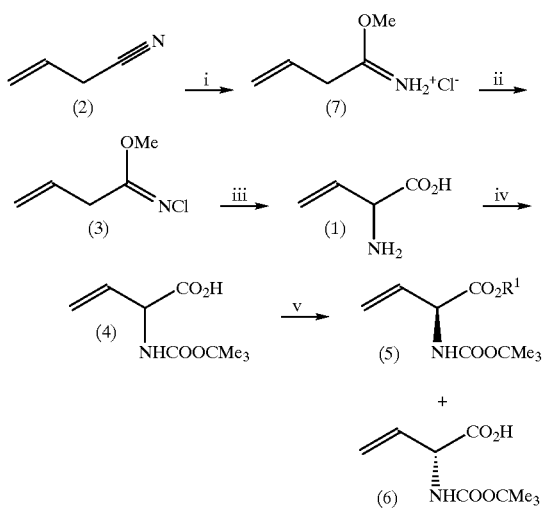

Reagents i, MeOH/HCl; ii, NaOCl; iii, OH/H$_2$O; iv, (Me$_3$OCO)$_2$O/OH; v, papain, H$_2$O/EtOAc, R$^1$OH.

The first step according to scheme 1 is the conversion of the cheap readily available allyl cyanide into the Pinner product Methyl-3-butenylimidate hydrochloride (7)—by reacting allyl cyanide and anhydrous methanol in the molar ratio of 1:1 to 1:5 and in the presence of hydrochloric acid at temperatures between −20° C. and +20° C. A reaction temperature between −10 and +10° C. is preferred. The product resulting from this first reaction is converted into methyl N-chloro-3-butenylimidate (3) with sodium hypochlorite. The sodium hypochlorite solution can be used in excess, preferred is an equimolar amount up to a two fold molar excess of sodium hypochlorite. The reaction temperature may be in the range of −40 to +40° C., preferably between −10 and +10° C. The product methyl-N-chloro-3-butenylimidate can be isolated by extraction with a water insoluable organic solvent, e.g. CHCl$_3$, EtOAc, diethylether, light petroleum, hexane, and further more. The methyl-N-chloro-3-butenylimidate (3) is converted via a Neber-like reaction into vinyl glycine (1) via reacting (3) with aqueous sodium-hydroxide. The reaction temperature for this step can be in the range of −20° C. up to refluxing temperature, preferentially in the range of −10° C. to +40° C. The reaction time is in the range of 5 to 25 h, preferentially 10 h. The product vinyl glycine can be isolated using well known techniques such as crystallisation or chromatography, e.g. using a cation exchange resin.

It is also feasible to convert the vinyl glycine (1) prepared by the above mentioned reaction sequence in situ directly into the N-tert-butyloxy (BOC) derivative. Therefore the N-chloro-3-butenylimidate (3) is converted with aqueous sodium hydroxide according to the above described procedure into vinyl glycine and after the reaction time of 5 to 25 h, preferentially 10 h, a water insoluble organic solvent is added, preferably dioxan. The mixture is cooled to −10° C. to 10° C. and di-tert-bytylcarbonate in the molar ratio of 1 to 15 is added. The reaction mixture is stirred for another 5 to 50 h, while the reaction temperature may rise up to 30° C., preferentially to room temperature. The product (4) can be isolated according to well known techniques, e.g. by adding a water immiscible organic solvent, e.g. ethyl acetate, to the reaction mixture, carefully adjusting the pH of the aqueous solution to pH 2–6 and extracting the product into the organic phase. The organic extracts are evaporated to dryness to give the N-butoxycarbonyl vinyl glycine (4).

The resolution of the N-tert.butyloxycarbonyl vinyl glycine (4) can be carried out using an enantioselective enzymatic conversion of L-(4) into a corresponding ester (5) while D-(4) remains unesterified.

For this purpose D,L-(4) is dissolved in a mixture of a water immiscible organic solvent, e.g. hexane, dichloromethane etc., and the alcohol component R$^1$OH with R=linear or branched C$_1$–C$_8$-alkyl, preferentially C$_1$–C$_4$-alkyl, most preferentially C$_2$-alkyl.

The solution is given to an aqueous buffer of pH 2–6, preferentially 4–5. Suitable enzymes are hydrolytic enzymes such as lipases, esterases and proteinases which are able to convert selectively one of the two enantiomers of a racemic N-protected amino acid. Preferred are proteases, most preferred thiol proteinases e.g. papain [E. C. 3.4.22.2].

In order to circumvent an unfavorable equilibrium constant when the esterification is performed in a partly aqueous medium the enzymatic esterification is carried out in a two phase system.

The product of esterification is preferentially partitioned into the organic phase, relative to the substrate. The new effective equilibrium constant is a function of the partition coefficients of substrate and product between water and the organic solvent, and of the volumes of the two phases.

For resolution of the Boc-derivative (4) with papain an organic phase of ethyl acetate and the esterifying alcohol ethanol was preferred. The reaction temperature is maintained between 15 and 50° C., preferentially at temperatures between 20 and 40° C.

The optimum reaction time depends on the reaction conditions and can easily be identified by pursuing the reaction using conventional analytical techniques (DC, HPLC etc.).

The isolation of the products proceeds via separating the organic layer from the aqueous phase, and washing the organic layer with aqueous sodium hydrogen carbonate. The organic layer is evaporated to dryness to give the crude Ethyl-L-N-protected vinyl glycine in high chemical ad optical yield of >90% which can be purified using conventional technique, e.g. chromatography. In order to isolate the D-N-protected vinyl glycine, the aqueous sodium hydrogen carbonate solution is brought to pH 1–5, preferentially 2–4 and extraced with an organic solvent. After evaporation of the organic solvent to dryness the crude D-N-protected vinyl glycine (4) is obtained in high yield and purity.

The method disclosed here thus provides a simple, inexpensive route to either L- or D-vinyl glycine in enantiomerically pure form (which is useful as a chiral synthon).

The instant invention concerns a method to synthesice vinyl glycine (I) via a 3 step pathway, starting with vinyl cyanide including a Pinner reation and Neber rearrangement and leading to the racemate of (I). The racemic mixture may then be resolved as the Boc derivative to both L- and D-isomers using papain respective other suitable enzymes.

The invention is further described in the examples and claims.

In the following examples $^1$H n.m.r. was carried out at 200 MHz using a Perkin Elmer R34 spectrometer, at 250 Mhz using a Bruker AC 250 spectrometer, or at 400 MHz using a Bruker WH400 spectrometer. $^{13}$C N.m.r. spectra were determined at 100.62 MHz using a Bruker WH400 spectrometer. Mass spectra were determined using a Krator MS 80 mass spectrometer.

EXAMPLES

1. Methyl 3-butenylimidate hydrochloride (7)

Into a stirred solution of allyl cyanide (3-butenenitrile ((2); 10 g, 15.2 mmol) in anhydrous methanol (10 ml) under nitrogen at 0° C. was passed dry HCl gas for 1 h. The flask was stoppered and its contents were stirred for 12 h at 2° C. The reaction mixture was diluted with dry diethyl ether (250 ml), the resulting precipitate was filtered off and again washed with diethyl ether (50 ml) to give the imidate hydrochloride (7) as a colourless hyrogroscopic solid (19,28 g, 95%. $\delta_H$ (220 MHz; D$_2$O) 5.9 (1 H, m, CH=CH$_2$), 5.25 (1 H, br. d, J 16 Hz, CH=CHH trans), 5.25 (1 H, br. d, J 12 Hz, CH=CHH cis), 3.7 (3 H, s, OCH$_3$), 3.17 ppm (2 H, d, J 12 Hz, CH$_2$).

$\nu$max (nujol mull)/cm$^{-1}$ 1669 (C=N).

m/z (Cl) 136 ((M+1)$^+$, 10.1%), 122 (5.4), 100 ((M—HCl)$^+$, 100), 86 ((M—HCl—CH$_3$)$^+$, 47.1), 68 (2.0). m/z (El) 235 ((M—HCl)$^+$, 2.5%), 202 ((2M+2-2HCl)$^+$, 7.1), 185 ((2M+1-HCl —CH$_3$)$^+$, 16.9), 136 ((M+1)$^+$, 28.7), 110 (39.7), 100 ((M—HCl)$^+$, 100), 93 ((2M+1-2HCl—CH$_3$)$^+$, 63.7), 86 ((M+1-HCl—CH$_3$)$^+$, 1.2).

2. Methyl N-chloro-3-butenylimidate (3)

The imidate hydrochloride (7) (3.0 g) was added directly to sodium hypochlorite solution (12–14%, 100 ml) at 0° C. The mixture was stirred for 1 h and extracted with light petroleum (b.p. 40–60° C., 3×30 ml). The extracts were dried (MgSO$_4$) and concentrated under reduced pressure to give the N-chloroimidate (3) as a colourless oil (2.95 g, 100%). $\delta_H$ (220 MHz; CDCl$_3$) 5.9 (1 H, m, CH=CH$_2$), 5.28 (1 H, d, J 17 Hz, CH=CHH trans), 5.25 (2 H, d, J 11 Hz, CH=CHH cis), 3.85 (3 H, s, OCH$_3$), 3.4 ppm (2 H, d J 12 Hz, CH$_2$). m/z (El) 134 ((M+1)$^+$, 6.9%), 98 ((M—HCl)$^+$, 20.6), 92 (17), 83 (0.7), 69 (100).

3. D,L-Vinyl glycine (1)

A solution of N-chloroimidate (3) (0.88 g, 6.6 mmol) in sodium hydroxide solution (0.79 g, 19.8 mmol, 50 ml) was stirred for 10 h at room temperature. The solution was applied to a column of Dowex 50W-X8 cation exchange resin (H$^+$form, 10 g)). The column was washed with deionised water and eluted with 2% aqueous pyridine until the ninhydrin test was negative. The eluate was evaporated under reduced pressure to give DL-vinyl glycine (1) (0.35 g, 53%). M.p 175° C. (d). $\delta_H$ (220 MHz; D$_2$O) 5.9 (1 H, m, CH=CH$_2$), 5.45 (1 H, d, J 15.7 Hz, CH=CHH trans, 5.43 (1 H, d, J 12.5 Hz, CH=CHH cis), 4.3 ppm (1 H, d, J 9 Hz, CH—CH=CH$_2$). $\delta_C$ (100 MHz, D$_2$O) 173.7 (C1), 131.0 (C3), 122.1 (C4), 57.8 (C2). m/z (Cl) 102 86 ((M+1)$^+$, 20.1%), 58 ((M+1-CO$_2$)$^+$, 1.1), 56 (9.1) (Found M+1$^+$: 102.0555 for C$_4$H$_8$NO$_2$, requires 102.111).

4. N-tert-butyloxycarbonyl-D,L-vinyl glycine (4)

A solution of freshly prepared N-chloroimidate ((3); 1.1 g,) in a solution of sodium hydroxide (1.079 g) in water (50 ml) was stirred at room temperature for 10 h. Dioxan (50 ml) was added, the mixture was cooled to 0° C., di-tert-butyldicarbonate (2.14 g) was added and the mixture was stirred for 8 h with the cooling source removed so that the temperature gradually increased to room temperature. The dioxan was removed under reduced pressure and the remaining solution was extracted with ethyl acetate (10 ml). To the aqueous phase was added ethyl acetate (15 ml). The aqueous phase was brought to pH 2 (1M KHSO$_4$) and extracted with the ethyl acetate following addition of a further 15 ml. The organic extracts were washed with saturated sodium chloride solution (15 ml), dried (MgSO$_4$) and concentrated under reduced pressure to give the derivative (4) as a colourless oil (1.11 g, 50%). $\delta_H$ (220 MHz; CDCl$_3$) 7.1 (1 H, m, NH), 6.0 (1 H, m, CH=CH$_2$), 5.45 (1 H, d, 19 Hz, CH=CHH trans), 5.30 (1 H, d, J 10 Hz, m, CH=CHH cis), 4,87 (1 H, m, CH$_2$), 1.41 (9H, s, t-Bu). $\delta_C$ (100 MHz, CDCl$_3$), 174.5, 173.5 (C1), 156.7, 1552 (C=O Boc), 132,6, 132,2 (C$_3$), 117.5 (C4), 81.6, 80.3 (C–Me$_3$ Boc), 57.0, 55.6 (C2), 28.1 (CH$_3$ Boc).

m/z (Cl) 202 (M+1)$^+$, 2.4%), 163 (20), 146 ((M—C$_4$H$_8$)$^+$, 6.5), 102 ((2M—CO$_2$C$_4$H$_8$)$^+$, 4.9), 86 (0.6). (Found M+1$^+$: 202.1067 for C$_9$H$_{16}$NO$_4$, requires 202,227).

m/z (Cl) 202 ((M+1)$^+$, 20.1%), 58 ((M+1-CO$_2$)$^+$, 1.1), 56 (9.1). V$_{max}$ (CHCl$_3$)/cm$^{-1}$ 1720, 1510, 1465.

5. Resolution of ethyl N-tert-butyloxycarbonylvinyl glycinate (4)

A mixture of papain (Sigma, type II, 0.3 g), L-cysteine (45 mg), EDTA tetrasodium salt (1 M, 75 µl) in citrate-phosphate buffer (1 M, 15 ml, pH 4.2) was stirred for 10 min. The racemic N-tert-butyloxycarbonyl-D,L-vinyl glycine ((4); 0.5 g, 2.5 mmol) dissolved in a mixture of dichloromethane (3 ml) and ethanol (2 ml) was added. The mixture was stirred for two days at 37° C. The mixture was filtered (celite®) and washed with ethyl acetate (10 ml) and water (10 ml). The organic phase was separated off, ethyl acetate (10 ml) was added and the aqueous phase was carefully acidified to pH 1 (Congo red) with KHSO$_4$ (1 M). The mixture was shaken, and the combined organic layer and washings were extracted with sodium hydrogen carbonate solution (5%, 2×5 ml), washed with water (10 ml) and saturated sodium chloride solution (10 ml), dried (MgSO$_4$) and concentrated under reduced pressure. The residue was purified by flash chromatography with light petroleum (b.p. 40–60° C.):ethyl acetate (10:1, v/v) as eluent to give ethyl L-N-tert-butyloxycarbonylvinyl glycinate (5) as an oil (0.2 g, 70%). $\delta_H$ (400 MHz; CDCl$_3$) 5.83 ) (1 H, ddd, J 17, 14, 7 Hz, CH=CH$_2$), 5.35 (1 H, dd, 17.1, 8 Hz, CH=CHH trans), 5.30 (1 H, dd, J 10.3, 1.7 Hz, CH=CHH cis), 4.8 (1 H, m, CH), 4.17 (2 H, q, J 7.1 Hz, CH$_2$CH$_3$), 1.41 (9H, s, ti-Bu), 1.23 (3 H, t, J 7.1 Hz, CH$_2$CH$_3$).

$\delta_C$ (100 MHz, CDCl$_3$) 170.6 (C$_1$), 154.7, 155.2 (C=O Boc), 132.7 (C3), 117.0 (C4), 79.9 (C–Me$_3$ Boc), 61.6 (C$_2$), 55.7 (CH$_2$Et), 28.1 (CH$_3$ Boc), 14.0 (CH$_3$Et). m/z (Cl) 230 ((M+1)$^+$, 0.8%), 174 ((M+1–C$_4$H$_8$)$^+$, 18.2), 156 (13.8), 130 ((M+1–C$_4$H$_8$–CO$_2$)$^+$, 9.2), 100 ((M+1–C$_4$H$_8$–CO$_2$–C$_2$H$_5$)$^+$, 23.1), 156 (2.8%), (Found M+1$^+$: 230.1394 for C$_{11}$H$_{20}$NO$_4$, requires 230.277). $V_{max}$ (CHCl$_3$)/cm$^{-1}$ 1770, 1712, 1495 cm$^{-1}$.

The organic layer was washed with saturated sodium chloride solution (10 ml), dried (MgSO$_4$) and concentrated under reduced pressure to give D-N-tert-butyloxycarbonyl vinylglycine 6 (0.24 g, 90%).

Boc-deprotection using standard reaction conditions (trifluoro acetic acid) gives the corresponding amino acids with high enantiomeric purity:

L-Vinyl glycine {(S)-2-amino-3-butenoic acid}: $[\alpha]_D$=+94.7° (H$_2$O, 25.8° C., c=0.25).

D-vinyl glycine {(R)-2-amino-3-buenoic acid}: $[\alpha]_D$=−96.3° (H$_2$O, 22.9° C., c=0.46).

What is claimed is:

1. A method of producing vinyl glycine comprising:
    (a) reacting allyl cyanide with anhydrous methanol in a molar ratio of 1:1 to 1:5 and in the presence of hydrochloric acid at a temperature from −20° C. to 20° C. to form methyl-3-butenylimidate hydrochloride;
    (b) reacting the methyl-3-butenylimidate hydrochloride formed in step (a) with sodium hypochlorite at a temperature from −40° C. to 40° C. to form methyl-N-chloro-3-butenylimidate; and
    (c) reacting the methyl-N-chloro-3-butenylimidate formed in step (b) with aqueous hydroxide at a temperature from −20° C. up to refluxing temperature for 5 to 25 hours to form vinyl glycine.

2. A method of producing L- or D-vinyl glycine in enantiomerically pure form by extending the steps of claim 1 comprising:
    (d) reacting the vinyl glycine formed in step (c) with di-tert-butylcarbonate to form N-tert-butoxycarbonyl vinyl glycine; and
    (e) enantioselectively esterifying the N-tert-butoxycarbonyl vinyl glycine formed in step (d) with an alcohol of the formula R$^1$OH in the presence of a hydrolytic enzyme where R$^1$ is a linear or branched C$_1$–C$_8$-alkyl.

3. A method according to claim 2, where the hydrolytic enzyme is a lipase, esterase or proteinase.

4. A method according to claim 3, where the hydrolytic enzyme is a proteinase.

5. A method according to claim 4, where the proteinase is a thiol proteinase.

* * * * *